United States Patent [19]
Koenig et al.

[11] 4,439,369
[45] * Mar. 27, 1984

[54] HALOGENATED, TERTIARY DIISOCYANATES AND THEIR PREPARATION

[75] Inventors: Karl-Heinz Koenig, Frankenthal; Volker Schwendemann, Wiesenbach, both of Fed. Rep. of Germany

[73] Assignee: BASF Aktiengesellschaft, Ludwigshafen, Fed. Rep. of Germany

[*] Notice: The portion of the term of this patent subsequent to Jun. 15, 1999 has been disclaimed.

[21] Appl. No.: 330,090

[22] Filed: Dec. 14, 1981

[30] Foreign Application Priority Data

Jan. 23, 1981 [DE] Fed. Rep. of Germany ....... 3102089

[51] Int. Cl.³ ................. C07C 118/00; C07C 119/045

[52] U.S. Cl. ........................... 260/453 P; 260/453 A; 260/453 AP

[58] Field of Search ......... 260/453 A, 453 AP, 453 P

[56] References Cited

U.S. PATENT DOCUMENTS 4,344,891  8/1982  Koenig et al. .................. 260/453 A

*Primary Examiner*—Dolph H. Torrence
*Attorney, Agent, or Firm*—John H. Shurtleff

[57] ABSTRACT

Halogenated, tertiary diisocyanates and a process for their preparation by reacting tertiary diisocyanates with halogen, sulfuryl chloride and/or sulfuryl bromide.

The halogenated, tertiary diisocyanates which can be prepared by the process according to the invention are valuable starting materials for the preparation of pest control agents, fatliquors, drugs, flameproofing agents, lubricating oils, synthetic resins and lubricants.

8 Claims, No Drawings

HALOGENATED, TERTIARY DIISOCYANATES AND THEIR PREPARATION

The present invention relates to halogenated, tertiary diisocyanates and a process for their preparation by reacting tertiary diisocyanates with halogen, sulfuryl chloride and/or sulfuryl bromide.

Halogenation of aliphatic isocyanates with at least one replaceable hydrogen on the carbon in the α-position relative to the nitrogen of the isocyanate group has been disclosed (German Patent 1,122,058 and Angew. Chem. 74, (1962), 848–855 and 80, (1968), 942–953). German Patent 1,122,058 discloses that haloalkyl isocyanates are very reactive substances (column 2, lines 33 and 34), and that α-haloalkyl isocyanates tend to undergo condensation or polymerization (column 2, lines 30 and 31); in Example 3, relatively large quantities of distillation residues are obtained, in addition to a yield of 68%.

In the absence of solvents, halogenation of aliphatic isocyanates frequently leads to resinification and poor yields as a result of intramolecular condensation, as disclosed in Angew. Chem. (loc.cit., 946). This publication also discloses that large amounts of the corresponding carbamyl chloride are obtained as a result of adduct formation of the hydrogen chloride, formed in the reaction, with the isocyanate, and proposes the use of carbamyl chlorides as starting materials, in order to avoid this side reaction.

When the process for α-halogenation of aliphatic isocyanates disclosed in German Patent 1,122,058 is carried out industrially, it is found that a considerable amount of non-distillable residues of polymers or polycondensates, in general from about 20 to 40% by weight, based on the halogenated product, remain on distillation of the resulting mixture of isocyanates halogenated to various degrees.

We have found that halogenated, tertiary diisocyanates of the formula I

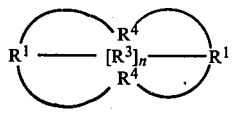

where n is 0 or 1 and the individual radicals $R^1$ are identical or different and, if n is 0, are

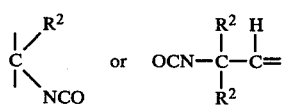

or, if n is 1, are

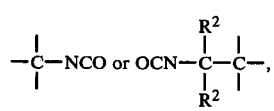

the individual radicals $R^2$ are identical or different and are aliphatic radicals, or two adjacent radicals $R^2$ linked by a carbon atom can be members of a halogen-free or halogenated alicyclic ring, and the individual radicals $R^3$ and $R^4$ can be identical or different and are aliphatic radicals, the end product having more halogen atoms than the starting material II, are obtained in an advantageous manner by halogenation of isocyanates by a process wherein a tertiary diisocyanate of the formula II

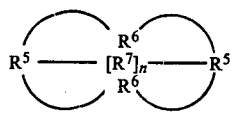

where $R^5$ has the meanings of $R^1$, $R^6$ has the meanings of $R^4$ and $R^7$ has the meanings of $R^3$, the above radicals overall having a smaller number of halogen atoms than $R^1$, $R^4$ and $R^3$ or being halogen-free, is reacted with halogen, sulfuryl chloride and/or sulfuryl bromide.

We have also found the novel halogenated tertiary diisocyanates of the formula I

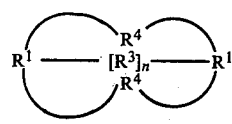

where n is 0 or 1 and the individual radicals $R^1$ are identical or different and, if n is 0, are

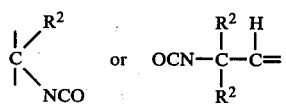

or, if n is 1, are

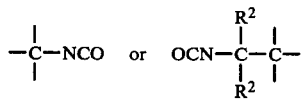

the individual radicals $R^2$ are identical or different and are aliphatic radicals, or two adjacent radicals $R^2$ linked by a carbon atom can be members of a halogen-free or halogenated alicyclic ring, and the individual radicals $R^3$ and $R^4$ can be identical or different and are aliphatic radicals.

If p-menthane diisocyanate and chlorine are used, the reaction is represented by the following equation:

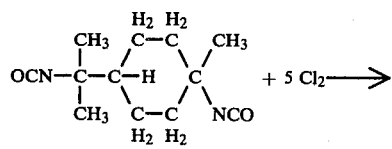

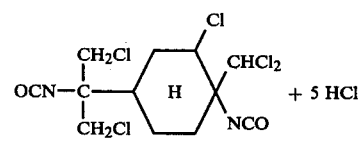

Compared to the prior art, the process according to the invention surprisingly gives halogenated, tertiary diisocyanates in a good yield and purity by a simple and economic route. It is surprising that defined substances are formed rather than a heterogeneous mixture of products in numerous stages of chlorination, and that only a small amount of distillation residue, if any, results.

Preferred starting materials II and hence preferred end products I are those where n is 0 or 1, the individual radicals $R^1$ are identical or different and, if n is 0, are

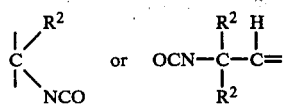

or, if n is 1, are

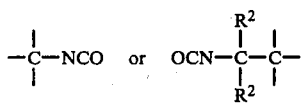

the individual radicals $R^2$ are identical or different and are halogen-free or halogenated alkyl of 1 to 6 carbon atoms, or two adjacent radicals $R^2$ linked via a carbon atom can be members of a halogen-free or halogenated alicyclic 5-, 6- or 7-membered ring, and the individual radicals $R^3$ and $R^4$ can be identical or different and are halogen-free or halogenated alkylene of 1 to 4 carbon atoms. Advantageously, the starting material II is halogen-free; it may, however, carry from 1 to 3 halogen atoms. $R^5$ has the meanings of $R^1$, $R^6$ has the meanings of $R^4$ and $R^7$ has the meanings of $R^3$, and each of $R^5$, $R^6$ and $R^7$ may differ from $R^1$, $R^4$ and $R^3$ by being halogen-free or having a lower degree of halogenation. Advantageously, the end product I contains from 1 to 10, in particular from 3 to 7, halogen atoms more than the starting material II. In general, at least one of the radicals $R^2$ carries one or more halogen atoms. Of the halogens, bromine and, in particular, chlorine are preferred.

Examples of suitable tertiary diisocyanates II are: 1,4-dimethyl-cyclohexane 1,4-diisocyanate and the corresponding 1,4-diethyl, 1,4-dipropyl, 1,4-diisopropyl, 1,4-dibutyl, 1,4-di-sec.-butyl, 1,4-diisobutyl and 1,4-di-tert.-butyl derivatives; similarly substituted 1,3- and 1,2-cyclohexane diisocyanates; p-menthane 1,4-diisocyanate and the homologous m-menthane 1,3-diisocyanates and o-menthane 1,2-diisocyanates; homologous compounds in which the 3-methyl groups are replaced by one or more identical or different radicals from the group consisting ethyl, propyl, isopropyl, butyl, isobutyl, sec.-butyl and tert.-butyl; dicyclo-[2,2,2]-hexane 1,4-diisocyanate and corresponding -[3,3,3]- nonane and -[2,1,2]-hexane derivatives; and cyclopentanes which are substituted in the 1,2- and 1,3-position and cycloheptanes which are substituted in the 1,2-, 1,3- and 1,4-position by methyl, ethyl, propyl, isopropyl, butyl, sec.-butyl, tert.-butyl or isobutyl and isocyanate. p-Menthane 1,4-diisocyanate are preferred.

The starting materials II are reacted with halogen, sulfuryl chloride or sulfuryl bromide as the halogenated agent, preferably with iodine, bromine or, in particular, chlorine. In general, mixtures of halogenated end products I containing different numbers of halogen substituents are obtained. First, the atoms in the β-position are preferentially halogenated. The main end product I in the mixture as a rule has a number of halogen substituents in the molecule which corresponds to the molar ratio of starting material to halogenating agent.

A stoichiometric amount of the starting material II can be used. Preferably, an excess of halogenating agent, based on the starting material II, is used for the preparation of disubstituted, trisubstituted and more highly halogenated alkyl isocyanates; not more than 15 moles, advantageously from 0.5 to 8 moles, more than the stoichiometric amount of halogenating agent per mole of starting material II can be used. Less than the stoichiometric amount of chlorine is advantageously used in the preparation of substantially monosubstituted compounds (partial chlorination); for example not more than 0.95 mole, advantageously from 0.6 to 0.9 mole, of halogenating agent is used per mole of starting material II. Circulatory halogenation in which elementary halogen which has not been consumed can be recycled is preferably used for more highly halogenated products. In general, the more rapidly the halogen is reacted, the smaller the excess of halogen can be. If sulfuryl halides are used, a catalytic amount, advantageously from 0.01 to 0.1% by weight, based on the halogenating agent, of a halogenation catalyst, such as benzoyl peroxide, azo-diisobutyronitrile or ascaridole, is advantageously added.

The reaction is preferably carried out with exposure to light, preferred sources of light being all those which emit visible radiation, for example sunlight or artificial light, for example from quartz lamps, mercury vapor lamps, daylight lamps or fluorescent tubes. Immersed lamps around which the reaction mixture flows are advantageously used, in particular in one of the vertical tubes of a circulatory apparatus. Sources of light which emit a high proportion of radiation in the wavelength range from 3,000 to 5,000 Angstroms are preferred.

The halogenation temperature is advantageously chosen in accordance with the degree of halogenation of the end product I. If low degrees of halogenation are desired, for example in the case of substitution of the starting materials II by 1 or 2 halogen atoms, it is therefore advantageous to start the reaction at from 0° to 10° C. and to increase the temperature slowly to about 50° C. If higher degrees of halogenation are desired, for example substitution of the starting materials II by from 3 to 6 halogen atoms, the reaction is started at from 50° to 100° C. and the temperature is increased more rapidly so that the uptake of halogen proceeds faster. As the degree of halogenation increases, it is advantageous to increase the temperature to not more than 230° C., preferably from 160° to 180° C., to maintain a sufficient halogen uptake. As a rule, the reaction is carried out at from −10° to 230° C., preferably from 40° to 180° C. and especially from 60° to 130° C., under atmospheric or superatmospheric pressure, by a continuous or batchwise procedure, preferably in the absence of added solvent.

The reaction can be carried out as follows:

The starting material II is reacted with the halogenating agent at the reaction temperature for 2 to 50 hours. If elementary halogen is used, this is added slowly and a little at a time throughout the period of reaction. The temperature is advantageously increased in the above manner and within the above temperature range during the reaction. If there is a single main end product, this is isolated from the reaction mixture in a conventional manner, for example by fractional distillation. In most cases, particularly in industrial operation, a mixture of end products is obtained, which can be purified by distillation but can usually be further processed directly, for example for the preparation of finishes, eg. flame-proofing agents. The isocyantes which have a low degree of halogenation and are obtained in the first runnings of the distillation can be re-used as intermediates for the synthesis or more highly halogenated fractions in a subsequent batch. The maximum uptake of halogen is from about 80 to 85% of theory.

The halogenated, tertiary diisocyanates which can be prepared by the process according to the invention are valuable starting materials for the preparation of pest control agents, fatliquors, drugs, flameproofing agents, lubricating oils, synthetic resins and lubricants. Thus, the polychlorinated diisocyanates can be used directly as bifunctional synthesis units for flameproof polymers, for example polyurethanes. Regarding use of the products, reference may be made to the above publications.

In the Example which follows parts are by weight.

EXAMPLE

Chlorination of p-menthane diisocyanate 222 parts of p-menthane diisocyanate (boiling point=86°-8°/0.1 mm Hg; $n_D^{24}=1.4720$) are dissolved in 500 parts of carbon tetrachloride and the solution is gassed with chlorine gas in a circulatory chlorinating apparatus, provided with a laboratory immersed lamp, at room temperature. The reaction is exothermic; gassing is continued until no further chlorine is taken up at the boiling point of the carbon tetrachloride. The solvent is then stripped off under reduced pressure and the colorless to light-yellow oil is chlorinated further at 120° C. until 115 parts of chlorine have been taken up. The crude product has a refractive index $n_D^{21}$ of 1.5260. Coarse fractional distillation gives the following fractions:

boiling point=125°-50°/0.4 mm Hg—7 parts (first runnings) $n_D^{21}=1.5140$ boiling point=157°-64°/0.4 mm Hg—130 parts $n_D^{21}=1.5160$ boiling point=165°-175°/0.4 mm Hg—110 parts $n_D^{21}=1.5225$ boiling point=175°-184°/0.4 mm Hg—59 parts $n_D^{21}=1.5300$ Fractions 2 and 3 contain 2 to 7 chlorine atoms per molecule of isocyanate.

We claim:

1. A process for the preparation of a halogenated, tertiary diisocyanate of the formula I

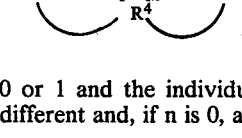

I where n is 0 or 1 and the individual radicals $R^1$ are identical or different and, if n is 0, are

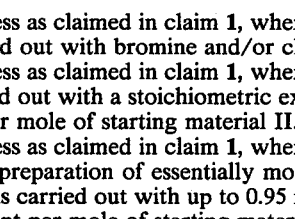

or, if n is 1, are the individual radicals $R^2$ are identical or different and are aliphatic radicals, or two adjacent radicals $R^2$ linked by a carbon atom can be members of a halogen-free or halogenated alicyclic ring, and the individual radicals $R^3$ and $R^4$ can be identical or different and are aliphatic radicals, the end product having more halogen atoms than the starting material II, by halogenation of an isocyanate, wherein a tertiary diisocyanate of the formula II

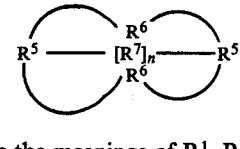

II where $R^5$ has the meanings of $R^1$, $R^6$ has the meanings of $R^4$ and $R^7$ has the meanings of $R^3$, the above radicals overall having a smaller number of halogen atoms than $R^1$, $R^4$ and $R^3$ or being halogen-free, is reacted with halogen, sulfuryl chloride and/or sulfuryl bromide.

2. A halogenated tertiary diisocyanate of the formula I

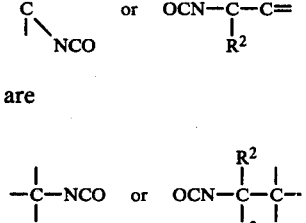

I where n is 0 or 1 and the individual radicals $R^1$ are identical or different and, if n is 0, are or, if n is 1, are the individual radicals $R^2$ are identical or different and are aliphatic radicals, or two adjacent radicals $R^2$ linked by a carbon atom can be members of a halogen-free or halogenated alicyclic ring, and the individual radicals $R^3$ and $R^4$ can be identical or different and are aliphatic radicals.

3. A process as claimed in claim 1, wherein the reaction is carried out with bromine and/or chlorine.

4. A process as claimed in claim 1, wherein the reaction is carried out with a stoichiometric excess of up to 15 moles per mole of starting material II.

5. A process as claimed in claim 1, wherein the reaction for the preparation of essentially monosubstituted compounds is carried out with up to 0.95 mole of halogenating agent per mole of starting material II.

6. A process as claimed in claim 1, wherein the reaction is carried out using a light source which emits a high proportion of radiation in the wavelength range from 3,000 to 5,000 Angstroms.

7. A process as claimed in claim 1, wherein the reaction is carried out at from −10° to +230° C.

8. A process as claimed in claim 1, wherein the reaction is carried out at from 40° to 180° C.

* * * * *